(12) United States Patent
Takano et al.

(10) Patent No.: US 8,269,044 B2
(45) Date of Patent: *Sep. 18, 2012

(54) METHOD FOR SELECTIVELY PRODUCING PRIMARY AMINE COMPOUND

(75) Inventors: Naoyuki Takano, Ibaraki (JP); Kazuyuki Tanaka, Oita (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1046 days.

This patent is subject to a terminal disclaimer.

(21) Appl. No.: 12/097,234

(22) PCT Filed: Dec. 14, 2006

(86) PCT No.: PCT/JP2006/324938
§ 371 (c)(1),
(2), (4) Date: Jun. 12, 2008

(87) PCT Pub. No.: WO2007/069685
PCT Pub. Date: Jun. 21, 2007

(65) Prior Publication Data
US 2009/0281325 A1    Nov. 12, 2009

(30) Foreign Application Priority Data
Dec. 15, 2005 (JP) ................. 2005-361489

(51) Int. Cl.
C07D 213/38 (2006.01)
C07D 251/04 (2006.01)
C07C 209/08 (2006.01)

(52) U.S. Cl. ............ 564/386; 544/193; 564/376

(58) Field of Classification Search .......... 544/193; 564/386, 376
See application file for complete search history.

(56) References Cited

U.S. PATENT DOCUMENTS

| 2,608,584 | A | 8/1952 | Sprules et al. |
| 5,210,303 | A | 5/1993 | Sugiyama |
| 7,439,357 | B2 * | 10/2008 | Takano et al. .......... 544/193 |
| 7,977,490 | B2 * | 7/2011 | Tanaka et al. .......... 548/202 |
| 2007/0197803 | A1 | 8/2007 | Takano et al. |

FOREIGN PATENT DOCUMENTS

| JP | 32-6256 B | 8/1957 |
| JP | 63-198654 A | 8/1988 |
| JP | 2908510 B2 | 6/1999 |
| JP | 3407082 B2 | 5/2003 |
| JP | 2006-290758 A | 1/2006 |
| JP | 2006-290758 A | 10/2006 |
| SU | 798102 A1 | 1/1981 |
| WO | WO-2005/123704 A1 | 12/2005 |
| WO | WO-2006/109811 A1 | 10/2006 |

OTHER PUBLICATIONS

M. S. Gibson, et al., The Gabriel Synthesis of Primary Amines, Angew. Chem. Internat. Edit., vol. 7, (1968), pp. 919-930.
Han Yinglin, et al., A Convenient Synthesis of Primary Amines Using Sodium Diformylamide as a Modified Gabriel Reagent, Synthesis, 1990, pp. 122-124.
Nikola Blazevic, et al., Hexamethylenetetramine, A Versatile Reagent in Organic Synthesis, Synthesis, 1979, pp. 161-176.
Chrisey et al., "Tris-N, N', N" (3', 4', 5'-Trimethoxyphenethyl)-1, 3, 5-Hexahydrotriazine, a Methylenemescaline Trimer: Characterization and Selective Cyclization to Anhalinine Under Non-Aqueous Conditions," Heterocycles, vol. 29, No. 6, 1989, pp. 1179-1183.
Chinese Office Action issued in the corresponding Chinese Patent Application No. 200680052617.1 on Aug. 18, 2011 (with English translation).
Japanese Office Action for Application No. 2006-336654 dated Mar. 13, 2012 (with English translation).

* cited by examiner

*Primary Examiner* — Venkataraman Balasubramanian
(74) *Attorney, Agent, or Firm* — Birch, Stewart, Kolasch & Birch, LLP

(57) ABSTRACT

Disclosed is a method for producing a primary amine compound represented by the formula (3):

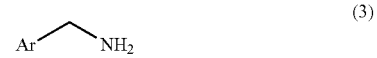

(3)

wherein, Ar is as defined below, which is characterized in that a halogen compound represented by the formula (1):

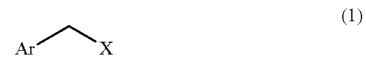

(1)

wherein, Ar represents an unsubstituted aromatic group such as a phenyl group, a naphthyl group, a pyridyl group, a furyl group, a thienyl group, a pyrrolyl group, an oxazolyl group, an isoxazolyl group or a pyrimidinyl group, or an aromatic group obtained by substituting such an unsubstituted aromatic group with 1-3 substituents; and X represents a halogen atom, ammonia and formaldehyde are reacted with each other, thereby obtaining a hexahydrotriazine compound represented by the formula (2):

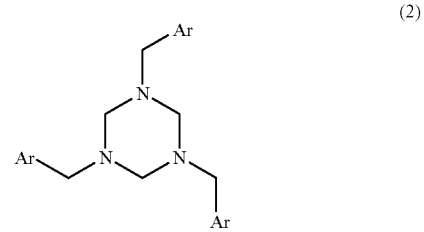

(2)

wherein, Ar is as defined above, and then the thus-obtained hexahydrotriazine compound is decomposed. By this method, a primary amine compound can be commercially advantageously produced by using a low-cost ammonia while suppressing production of a secondary amine as a by-product.

5 Claims, No Drawings

METHOD FOR SELECTIVELY PRODUCING PRIMARY AMINE COMPOUND

TECHNICAL FIELD

The present invention relates to a method for selectively producing a primary amine compound.

BACKGROUND ART

Hitherto, many selective synthesis methods for primary amine compounds have been reported, and examples thereof include a Gabriel reaction using phthalimide (for example, Non-Patent document 1) and a related reaction thereof (for example, Non-Patent document 2), a Delepine reaction using hexamethylene tetramine (for example, Non-Patent document 3), and the like. However, these methods are not exactly satisfactory from the industrial viewpoint because they require an expensive aminating agent or a complicated decomposition process. Although a synthesis method comprising use of ammonia, which is inexpensive, as an aminating agent is industrially useful, the method has difficulty in suppressing production of a secondary amine and requires 20 mol times or more of ammonia for selectively obtaining a primary amine (Patent document 1). Under the circumstances, a method of suppressing production of a secondary amine using coexistence of aromatic aldehyde has been proposed (Patent document 2). However, the method requires separation and recovery of aromatic aldehyde and therefore, is not satisfactory.

Non-Patent document 1: Angew. Chem. Int. Ed. Engl. Vol. 7, 919 (1968)
Non-Patent document 2: Synthesis 122 (1990)
Non-Patent document 3: Synthesis 161 (1979)
Patent document 1: U.S. Pat. No. 2,608,584, JP-B 32-6256
Patent document 2: Japanese Patent No. 2908510

DISCLOSURE OF THE INVENTION

Problems to be Solved by the Invention

Under the above-described situation, inventors of the present invention studied for development of a method for industrially advantageously producing a primary amine compound which comprises using inexpensive ammonia and suppressing production of a secondary amine as a by-product. As a result, they found that the desired primary amine compound could be produced by reacting a halogen compound with ammonia and formaldehyde, which is inexpensive and easily available, to convert the halogen compound into a hexahydrotriazine compound, and then subjecting the hexahydrotriazine compound to a decomposition treatment. Thus the present invention has been completed.

Means for Solving the Problems

The present invention provides a method for producing a primary amine compound represented by the formula (3):

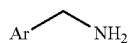 (3)

wherein Ar is as defined below, which comprises reacting a halogen compound represented by the formula (1):

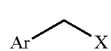 (1)

wherein Ar represents an aromatic group selected from the group consisting of a phenyl group, a naphthyl group, a pyridyl group, a furyl group, a thienyl group, a pyrrolyl group, an oxazolyl group, an isoxazolyl group, an isothiazolyl group, an imidazolyl group, a pyrazolyl group, a pyridazinyl group, a pyrimidinyl group, a pyrazinyl group, a quinolinyl group, a quinoxalinyl group and a benzimidazolyl group, and said Ar may have 1 to 3 substituents which may be the same or different and are independently a halogen atom, a lower alkyl group, a lower alkoxy group, a lower alkylenedioxy group, a nitro group, a cyano group or a di(lower alkyl)amino group, and X represents a halogen atom, with ammonia and formaldehyde to obtain a hexahydrotriazine compound represented by the formula (2):

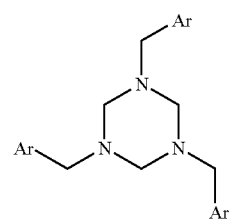 (2)

wherein Ar is as defined above, and subjecting the hexahydrotriazine compound represented by the formula (2) to a decomposition treatment.

Effect of the Invention

According to the present invention, it is possible to selectively and industrially advantageously produce a primary amine compound from a halogen compound and ammonia.

BEST MODE FOR CARRYING OUT THE INVENTION

First, a step of reacting the halogen compound represented by the formula (1) with ammonia and formaldehyde to obtain the hexahydrotriazine compound represented by the formula (2) (hereinafter referred to as the hexahydrotriazine compound (2)) is explained.

In the formula of the halogen compound (1), the aromatic group represented by Ar may have 1 to 3 substituents. Examples of the substituent include a halogen atom, a lower alkyl group, a lower alkoxy group, a lower alkylenedioxy group, a nitro group, a cyano group, and a di(lower alkyl)amino group. Examples of the halogen atom include a fluorine atom, a chlorine atom, a bromine atom, and an iodine atom. Examples of the lower alkyl moiety of the lower alkyl group, the lower alkoxy group and the di(lower alkyl)amino group include a C1-6 alkyl grou such as methyl, ethyl, propyl, butyl, pentyl, hexyl or the like. Examples of the lower alkylenedioxy group include a methylenedioxy group, an ethylenedioxy group, and the like. Examples of the halogen atom represented by X include a chlorine atom, a bromine atom, an iodine atom, and the like.

Examples of the halogen compound (1) include benzyl chloride, 2-chlorobenzyl chloride, 3-chlorobenzyl chloride, 4-chlorobenzyl chloride, 2-fluorobenzyl chloride, 3-fluorobenzyl chloride, 4-fluorobenzyl chloride, 2,4-dichlorobenzyl chloride, 3,4-dichlorobenzyl chloride, 2,6-dichlorobenzyl chloride, 2,4-difluorobenzyl chloride, 3,4-difluorobenzyl chloride, 2,6-difluorobenzyl chloride, 4-methylbenzyl chloride, 4-ethylbenzyl chloride, 2,4-dimethylbenzyl chloride, 4-t-butylbenzyl chloride, 3-methoxybenzyl chloride, 4-methoxybenzyl chloride, 4-cyanobenzyl chloride, 3-nitro-benzyl chloride, 4-N,N-dimethylamino-3-fluoro-benzyl chloride, benzyl bromide, 2-chlorobenzyl bromide, 3-chlorobenzyl bromide, 4-chlorobenzyl bromide, 2-fluorobenzyl bromide, 3-fluorobenzyl bromide, 4-fluorobenzyl bromide, 2,4-dichlorobenzyl bromide, 3,4-dichlorobenzyl bromide, 2,6-dichlorobenzyl bromide, 2,6-diflurobenzyl bromide, 4-methylbenzyl bromide, 4-ethylbenzyl bromide, 2,4-dimethylbenzyl bromide, 4-t-butylbenzyl bromide, 3-methoxybenzyl bromide, 4-methoxybenzyl bromide, 4-cyanobenzyl bromide, 1-chloromethylnaphthalene, 1-chloromethyl-2-methylnaphthalene, 2-naphthyl chloride, 1-naphthyl bromide, 2-naphthyl bromide, 2-chloromethylpyridine, 3-chloromethylpyridine, 4-chloromethylpyridine, 2-chloro-3-chloromethylpyridine, 2-chloro-4-chloromethylpyridine, 2-chloro-5-chloromethylpyridine, 2-chloro-6-chloromethylpyridine, 3-chloro-2-chloromethylpyridine, 3-chloro-4-chloromethylpyridine, 3-chloro-5-chloromethylpyridine, 3-chloro-6-chloromethylpyridine, 4-chloro-2-chloromethylpyridine, 4-chloro-3-chloromethylpyridine, 4-chloro-5-chloromethylpyridine, 4-chloro-6-chloromethylpyridine, 3-bromomethylpyridine, 2-chloro-5-bromomethylpyridine, 2-bromo-5-bromomethylpyridine, 3-iodomethylpyridine, 2-chloro-5-iodomethylpyridine, 2-iodo-5-iodomethylpyridine, 3-chloromethylfuran, 2-chloro-5-(chloromethyl)thiophene, 2-chloromethylpyrrole, 3-chloromethylpyrrole, 2-(chloromethyl)oxazole, 4-(chloromethyl)oxazole, 5-(chloromethyl)isoxazole, 5-(chloromethyl)isothiazole, 4-(chloromethyl)isothiazole, 4-(chloromethyl)-1H-imidazole, 2-(chloromethyl)-1H-imidazole, 5-(chloromethyl)pyrazole, 4-(chloromethyl)pyrazole, 4-(chloromethyl)pyridazine, 5-(chloromethyl)pyrimidine, 2-(chloromethyl)pyrazine, 2-(chloromethyl)quinoline, 7-chloro-2-chloromethylquinoline, 2-chloro-3-chloromethylquinoline, 2-(chloromethyl)-3-methylquinoxaline, 2-chloromethylbenzimidazole, 2-chloromethyl-5-chlorobenzimidazole, 3,4-methylenedioxybenzyl chloride, and the like.

As the ammonia, ammonia gas or liquid ammonia may be used. Alternatively, ammonia water may be used, or a solution of ammonia in an organic solvent prepared by dissolving ammonia in an organic solvent capable of dissolving ammonia, such as methanol, may be also used.

The amount of ammonia is usually 1 to 30 moles, preferably 2 to 25 moles, more preferably 2 to 10 moles per mole of the halogen compound (1).

As the formaldehyde, formaldehyde gas may be used. From the viewpoint of easy handling, paraformaldehyde or formalin is preferably used. The amount of formaldehyde is usually 1 to 10 moles, preferably 1 to 8 moles, more preferably 1 to 5 moles per mole of the halogen compound (1). It is preferable that the amount of ammonia to the amount of the halogen compound (1) is greater than that of formaldehyde.

The reaction temperature is usually 15° C. to 100° C., preferably 20° C. to 90° C. The reaction is usually performed under normal pressure or a pressurized condition of 0.5 MPa (gauge pressure) or below.

Although the reaction may be performed in the absence of a solvent, the reaction is preferably performed in an inert solvent. Examples of such solvent include an alcohol solvent such as methanol, ethanol, n-propanol, isopropanol or the like; an aromatic hydrocarbon solvent such as toluene, xylene or the like; a halogenated hydrocarbon solvent such as chlorobenzene, dichlorobenzene or the like; an aliphatic hydrocarbon solvent such as hexane, heptane, cyclohexane or the like; an ether solvent such as diethyl ether, tetrahydrofuran, dioxane or the like; an aprotic polar solvent such as acetonitrile, propionitrile, dimethylsulfoxide, N,N-dimethylacetamide or the like, and water, which may be a single solvent or a mixture of solvents. Among them, preferred are an alcohol solvent and water, and more preferred is an alcohol solvent. The amount of the solvent is usually 1 to 10 parts by weight per part by weight of the halogen compound (1).

The reaction is performed by mixing the halogen compound (1) with ammonia and formaldehyde to bring them into contact with each other. The order of mixing is not particularly limited. For example, the halogen compound (1), ammonia and formaldehyde may be mixed and reacted at a predetermined temperature. The halogen compound (1) and formaldehyde may be mixed, and then ammonia is added thereto to react. Ammonia and formaldehyde may be mixed, and then the halogen compound (1) may be added thereto to react. The halogen compound (1) and ammonia may be simultaneously added to formaldehyde. The halogen compound (1) and formaldehyde may be simultaneously added to ammonia.

The reaction may be performed, if necessary, in the co-presence of a phase-transfer catalyst such as a quaternary ammonium salt such as triethylbenzylammonium chloride, tri-n-octylmethylammonium chloride, trimethyldecylammonium chloride, tetramethylammonium bromide or tetra-n-butylammonium bromide, or crown ether.

The reaction appears to proceed through the formation of an unstable intermediate, a methyleneimine compound represented by the formula (4):

(4)

wherein Ar is as defined above, and trimerization of the methyleneimine compound represented by the formula (4) to produce the hexahydrotriazine compound (2).

After termination of the reaction, a reaction liquid containing the hexahydrotriazine compound (2) is obtained. The hexahydrotriazine compound (2) can be isolated, for example, by concentration of the reaction liquid. The hexahydrotriazine compound (2) can be also isolated by subjecting the reaction liquid as it is or the concentrated reaction liquid to an extraction treatment with water and a hydrophobic organic solvent and then concentrating the obtained organic layer. The hexahydrotriazine compound (2) can be also isolated as an acid addition salt such as a hydrochloride salt or a sulfate salt.

Examples of the hydrophobic organic solvent include a halogenated hydrocarbon solvent such as chloroform, chlorobenzene, dichlorobenzene or the like; an ester solvent such as ethyl acetate, butyl acetate or the like; a ketone solvent such as methyl ethyl ketone, methyl isobutyl ketone or the like; and an aromatic hydrocarbon solvent such as toluene, xylene or the like, which may be a single solvent or a mixture of solvents. The amount of the hydrophobic organic solvent is not particularly limited.

The reaction liquid or the organic layer containing the hexahydrotriazine compound (2) may be used in the decomposition treatment step described below without isolating the hexahydrotriazine compound (2) from the reaction liquid.

Examples of the hexahydrotriazine compound (2) thus obtained include 1,3,5-tris(benzyl)-1,3,5-hexahydrotriazine, 1,3,5-tris(2-chlorobenzyl)-1,3,5-hexahydrotriazine, 1,3,5-tris(3-chlorobenzyl)-1,3,5-hexahydrotriazine, 1,3,5-tris(4-chlorobenzyl)-1,3,5-hexahydrotriazine, 1,3,5-tris (2-fluorobenzyl)-1,3,5-hexahydrotriazine, 1,3,5-tris(3-fluorobenzyl)-1,3,5-hexahydrotriazine, 1,3,5-tris(4-fluorobenzyl)-1,3,5-hexahydrotriazine, 1,3,5-tris(2,4-dichlorobenzyl)-1,3,5-hexahydrotriazine, 1,3,5-tris(3,4-dichlorobenzyl)-1,3,5-hexahydrotriazine, 1,3,5-tris(2,6-dichlorobenzyl)-1,3,5-hexahydrotriazine, 1,3,5-tris(2,4-difluorobenzyl)-1,3,5-hexahydrotriazine, 1,3,5-tris(3,4-difluorobenzyl)-1,3,5-hexahydrotriazine, 1,3,5-tris(2,6-difluorobenzyl)-1,3,5-hexahydrotriazine, 1,3,5-tris(4-methylbenzyl)-1,3,5-hexahydrotriazine, 1,3,5-tris(4-ethylbenzyl)-1,3,5-hexahydrotriazine, 1,3,5-tris(2,4-dimethylbenzyl)-1,3,5-hexahydrotriazine, 1,3,5-tris(4-t-butylbenzyl)-1,3,5-hexahydrotriazine, 1,3,5-tris(3-methoxybenzyl)-1,3,5-hexahydrotriazine, 1,3,5-tris(4-methoxybenzyl)-1,3,5-hexahydrotriazine, 1,3,5-tris(4-cyanobenzyl)-1,3,5-hexahydrotriazine, 1,3,5-tris(3-nitrobenzyl)-1,3,5-hexahydrotriazine, 1,3,5-tris(4-N,N-dimethylamino-3-fluorobenzyl)-1,3,5-hexahydrotriazine, 1,3,5-tris{(1-naphthyl)methyl}-1,3,5-hexahydrotriazine, 1,3,5-tris{(2-methyl-1-naphthyl)methyl}-1,3,5-hexahydrotriazine, 1,3,5-tris{(2-naphthyl)methyl}-1,3,5-hexahydrotriazine, 1,3,5-tris{(2-pyridyl)methyl}-1,3,5-hexahydrotriazine, 1,3,5-tris{(3-pyridyl)methyl}-1,3,5-hexahydrotriazine, 1,3,5-tris{(4-pyridyl)methyl}-1,3,5-hexahydrotriazine, 1,3,5-tris{(2-chloropyridin-3-yl)methyl}-1,3,5-hexahydrotriazine, 1,3,5-tris{(2-chloropyridin-4-yl)methyl}-1,3,5-hexahydrotriazine, 1,3,5-tris{(2-chloropyridin-5-yl)methyl}-1,3,5-hexahydrotriazine, 1,3,5-tris{(2-chloropyridin-6-yl)methyl}-1,3,5-hexahydrotriazine, 1,3,5-tris{(3-chloropyridin-2-yl)methyl}-1,3,5-hexahydrotriazine, 1,3,5-tris{(3-chloropyridin-4-yl)methyl}-1,3,5-hexahydrotriazine, 1,3,5-tris{(3-chloropyridin-5-yl)methyl}-1,3,5-hexahydrotriazine, 1,3,5-tris{(3-chloropyridin-6-yl)methyl}-1,3,5-hexahydrotriazine, 1,3,5-tris{(4-chloropyridin-2-yl)methyl}-1,3,5-hexahydrotriazine, 1,3,5-tris{(4-chloropyridin-3-yl)methyl}-1,3,5-hexahydrotriazine, 1,3,5-tris{(4-chloropyridin-5-yl)methyl}-1,3,5-hexahydrotriazine, 1,3,5-tris{(4-chloropyridin-6-yl)methyl}1,3,5-hexahydrotriazine, 1,3,5-tris{(2-bromopyridin-5-yl)methyl}-1,3,5-hexahydrotriazine, 1,3,5-tris{(2-iodopyridin-5-yl)methyl}-1,3,5-hexahydrotriazine, 1,3,5-tris{(3-furyl)methyl}-1,3,5-hexahydrotriazine, 1,3,5-tris{(2-chloro-5-thienyl)methyl}-1,3,5-hexahydrotriazine, 1,3,5-tris{(2-pyrrolyl)methyl}-1,3,5-hexahydrotriazine, 1,3,5-tris{(3-pyrrolyl)methyl}-1,3,5-hexahydrotriazine, 1,3,5-tris{(2-oxazolyl)methyl}-1,3,5-hexahydrotriazine, 1,3,5-tris{(4-oxazolyl)methyl}-1,3,5-hexahydrotriazine, 1,3,5-tris{(5-isoxazolyl)methyl}-1,3,5-hexahydrotriazine, 1,3,5-tris{(5-isothiazolyl)methyl}-1,3,5-hexahydrotriazine, 1,3,5-tris{(4-isothiazolyl)methyl}-1,3,5-hexahydrotriazine, 1,3,5-tris{(1H-imidazol-4-yl)methyl}-1,3,5-hexahydrotriazine, 1,3,5-tris{(1H-imidazol-2-yl)methyl}-1,3,5-hexahydrotriazine, 1,3,5-tris{(5-pyrazolyl)methyl}-1,3,5-hexahydrotriazine, 1,3,5-tris{(4-pyrazolyl)methyl}-1,3,5-hexahydrotriazine, 1,3,5-tris{(4-pyridazinyl)methyl}-1,3,5-hexahydrotriazine, 1,3,5-tris{(5-pyrimidinyl)methyl}-1,3,5-hexahydrotriazine, 1,3,5-tris{(2-pyrazinyl)methyl}-1,3,5-hexahydrotriazine, 1,3,5-tris{(2-quinolinyl)methyl}-1,3,5-hexahydrotriazine, 1,3,5-tris{(7-chloroquinolin-2-yl)methyl}-1,3,5-hexahydrotriazine, 1,3,5-tris{(2-chloroquinolin-3-yl)methyl}-1,3,5-hexahydrotriazine, 1,3,5-tris{(3-methylquinoxalin-3-yl)methyl}-1,3,5-hexahydrotriazine, 1,3,5-tris{(3-methylquinoxalin-2-yl)methyl}-1,3,5-hexahydrotriazine, 1,3,5-tris{(2-benzimidazolyl)methyl}-1,3,5-hexahydrotriazine, 1,3,5-tris{(5-chlorobenzimidazol-2-yl)methyl}-1,3,5-hexahydrotriazine, 1,3,5-tris(3,4-methylenedioxybenzyl)-1,3,5-hexahydrotriazine, and the like.

Next, a step of subjecting the hexahydrotriazine compound (2) thus obtained to a decomposition treatment to produce the primary amine compound represented by the formula (3) (hereinafter referred to as the primary amine compound (3)) is explained.

Examples of a method for the decomposition treatment include two methods, namely, a hydrolysis treatment and a hydroxylamine treatment. First, a step of the hydrolysis treatment is described.

In this step, the hexahydrotriazine compound (2) obtained in the preceding step is converted into the primary amine compound (3) by hydrolysis. This step is usually performed by contacting and mixing the hexahydrotriazine compound (2) with an aqueous solution of an acid. Examples of the aqueous solution of an acid include an aqueous solution of hydrochloric acid, sulfuric acid, phosphoric acid, nitric acid or the like. Preferred is an aqueous solution of hydrochloric acid or sulfuric acid.

The acid concentration of the aqueous solution of an acid is not particularly limited. The used amount of an acid is usually 1 to 10 moles, preferably 1 to 5 moles per mole of the hexahydrotriazine compound (2).

The hydrolysis treatment may be performed after, as described above, the hexahydrotriazine compound (2) produced in the preceding step is isolated from the reaction liquid. Alternatively, the reaction liquid or the organic layer containing the hexahydrotriazine compound (2) may be subjected to the hydrolysis treatment without isolating the hexahydrotriazine compound (2).

The temperature for the hydrolysis treatment is usually 10 to 100° C., preferably 25 to 70° C.

As the hydrolysis of the hexahydrotriazine compound (2) progresses, formaldehyde is produced as a by-product. For the purpose of facilitating removal of the by-produt formaldehyde, it is preferable that the hydrolysis treatment of the hexahydrotriazine compound (2) is performed in the presence of a lower alcohol compound to perform hydrolysis of the hexahydrotriazine compound (2) and acetalization of the by-product formaldehyde at the same time. Examples of the lower alcohol compound include lower alcohol compounds having 1 to 4 carbon atoms, such as methanol, ethanol or the like. The amount of the lower alcohol compound is usually 1.5 moles or more, preferably 2 moles or more, more preferably 2.5 moles or more per mole of the hexahydrotriazine compound (2), and there is no upper limit of the amount. In the case where a reaction liquid containing the hexahydrotriazine compound (2) is used as it is and the reaction liquid also contains a lower alcohol compound, the amount of the lower alcohol compound that may be used is determined in consideration of the amount of the lower alcohol compound contained in the reaction liquid. In addition, formaldehyde may remain in the reaction liquid in some cases. In such case, the lower alcohol compound may be used in an amount sufficient to accomplish acetalization of not only the by-product formaldehyde but also the formaldehyde remaining in the reaction liquid. Of course, the acetalization of formaldehyde may be performed after the hydrolysis treatment of the hexahydrotriazine compound (2).

After termination of the hydrolysis treatment, the primary amine compound (3) or an acid addition salt thereof can be isolated, for example, by concentration of a reaction liquid. The primary amine compound (3) can be also isolated by concentrating a reaction liquid, extracting the concentrated reaction liquid with alkaline water and a hydrophobic organic solvent, and then concentrating the obtained organic layer. Examples of the alkaline water include an aqueous solution of alkali metal hydroxide such as an aqueous solution of sodium hydroxide, or the like. The amount of the alkaline water is adjusted so that an aqueous layer can have usually pH 8 to 14, preferably pH 10 to 14 during the extraction treatment.

Then, the step of the hydroxylamine treatment is described.

In this step, the hexahydrotriazine compound (2) is treated with hydroxylamine under an acidic condition to produce the primary amine compound (3). This step is usually performed by contacting and mixing the hexahydrotriazine compound (2) and hydroxylamine under an acidic condition.

Examples of the hydroxylamine that may be used include hydroxylamine in a free form, and an acid addition salt of hydroxylamine, such as hydroxylamine hydrochloride ($NH_2OH.HCl$), hydroxylamine sulfate (($NH_2OH)_2.H_2SO_4$) and the like. Such hydroxylamine is commercially available. Such hydroxylamine may be used as it is or may be used as a solution such as an aqueous solution.

The amount of the hydroxylamine is usually 1 to 30 moles, preferably 1 to 15 moles, more preferably 1 to 10 moles per mole of the hexahydrotriazine compound (2).

The hexahydrotriazine compound (2) and hydroxylamine are contacted and mixed usually in an aqueous solvent or a mixture of solvents containing water and an organic solvent, under an acidic condition. The amount of water or a mixture of solvents containing water and an organic solvent is usually 0.5 to 20 parts by weight per part by weight of the hexahydrotriazine compound (2). In the case of using a mixture of solvents containing water and an organic solvent, the ratio of water and the organic solvent to be mixed is not particularly limited. Examples of the organic solvent include an aromatic hydrocarbon solvent such as toluene, xylene or the like; a halogenated hydrocarbon solvent such as chloroform, chlorobenzene, dichlorobenzene or the like; an ether solvent such as diethyl ether, diisopropyl ether, methyl tert-butyl ether, tetrahydrofuran or the like; and an alcohol solvent such as methanol, ethanol, isopropanol or the like.

Examples of the acid used for the hydroxylamine treatment under an acidic condition include a mineral acid such as hydrochloric acid, sulfuric acid, phosphoric acid or the like; and an organic carboxylic acid such as acetic acid, propionic acid, citric acid or the like. Preferred is mineral acid, and hydrochloric acid or sulfuric acid is more preferred. The amount of the acid that may be used is not particularly limited as long as hydroxylamine and the hexahydrotriazine compound (2) can be contacted and mixed under an acidic condition.

Hydroxylamine may be added to the hexahydrotriazine compound (2), or the hexahydrotriazine compound (2) may be added to hydroxylanine. The temperature of the hydroxylamine treatment is usually 0 to 100° C., preferably 0C to 50° C.

The hexahydrotriazine compound (2) is treated with hydroxylamine under an acidic condition and then, if necessary, kept for a predetermined period to obtain a solution containing an acid addition salt of the primary amine compound (3). The acid addition salt of the primary amine compound (3) can be isolated, for example, by concentration of the solution.

When the hexahydrotriazine compound (2) is treated with hydroxylamine under an acidic condition, formaldoxime or a trimer thereof which is produced by the reaction between the above hydroxylamine and formaldehyde is produced together with an acid addition salt of the primary amine compound (3). Therefore, it is preferable that the obtained solution containing the acid addition salt of the primary amine compound (3) is subjected to an extraction treatment under a basic condition with, for example, a base and, if necessary, a hydrophobic organic solvent, to separate the solution into an organic layer containing the primary amine compound (3) and an aqueous layer containing formaldoxime or a trimer thereof. The organic layer thus obtained can be concentrated to isolate the primary amine compound (3) in higher purity. The isolated primary amine compound (3) may be converted into an acid addition salt thereof such as a hydrochloride salt by a reaction with an acid such as hydrochloric acid or the like. Examples of the base include alkali metal hydroxide such as sodium hydroxide or the like. The amount of the base is adjusted so that an aqueous layer can have usually pH 8 to 14, preferably pH 10 to 14 during the extraction treatment. Examples of the hydrophobic organic solvent include an aromatic hydrocarbon solvent such as toluene, xylene or the like; a halogenated hydrocarbon solvent such as chloroform, chlorobenzene, dichlorobenzene or the like; an ester solvent such as ethyl acetate, butyl acetate or the like; and a ketone solvent such as methyl ethyl ketone, methyl isobutyl ketone or the like, which may be a single solvent or a mixture of solvents. The amount of the hydrophobic organic solvent is not particularly limited.

Further, the organic layer containing the primary amine compound (3) obtained in the above described extraction treatment is mixed with an aqueous solution of an acid, and then subjected to a phase separation treatment to obtain an aqueous solution containing an acid addition salt of the primary amine compound (3). All or a part of the aqueous solution containing an acid addition salt of the primary amine compound (3) can be concentrated to isolate the acid addition salt of the primary amine compound (3). Alternatively, an insufficient solvent that hardly dissolves the acid addition salt of the primary amine compound (3) can be added to the aqueous solution containing an acid addition salt of the primary amine compound (3) to precipitate crystals of the acid addition salt of the primary amine compound (3). Examples of the aqueous solution of the acid include an aqueous solution of an acid such as hydrochloric acid, sulfuric acid, acetic acid, methanesulfonic acid or the like. The amount of the aqueous solution of the acid is adjusted so that the aqueous layer can have usually pH 2.5 to 5.5, preferably pH 3 to 5 during the extraction treatment. In the case where the obtained aqueous solution containing an acid addition salt of the primary amine compound (3) is colored, the aqueous solution may be decolorized by an addition of a decoloring agent such as activated carbon.

Examples of the primary amine compound (3) thus obtained include benzylamine, 2-chlorobenzylamine, 3-chlorobenzylamine, 4-chlorobenzylamine, 2-fluorobenzylamine, 3-fluorobenzylamine, 4-fluorobenzylamine, 2,4-dichlorobenzylamine, 3,4-dichlorobenzylamine, 2,6-dichlorobenzylamine, 2,4-difluorobenzylamine, 3,4-difluorobenzylamine, 2,6-difluorobenzylamine, 4-methylbenzylamine, 4-ethylbenzylamine, 2,4-dimethylbenzylamine, 4-t-butylbenzylamine, 3-methoxybenzylamine, 4-methoxybenzylamine, 4-cyanobenzylamine, 3-nitrobenzylamine, 4-N,N-dimethylamino-3-fluorobenzylamine, 1-aminomethylnaphthalene, 1-aminomethyl-2-methylnaphthalene, 2-aminomethylnaphthalene, 2-aminomethylpyridine, 3-aminomethylpyridine, 4-aminomethylpyridine, 2-chloro-3-aminomethylpyridine, 2-chloro-4-aminomethylpyridine, 2-chloro-5-aminomethylpyridine, 2-chloro-6-aminomethylpyridine, 3-chloro-2-aminomethylpyridine, 3-chloro-4-aminomethylpyridine, 3-chloro-5-aminomethylpyridine, 3-chloro-6-aminomethylpyridine, 4-chloro-2- aminomethylpyridine, 4-chloro-3-aminomethylpyridine, 4-chloro-5-aminomethylpyridine, 4-chloro-6-aminomethylpyridine, 2-bromo-5-aminomethylpyridine, 2-iodo-5-aminomethylpyridine, 3-aminomethylfuran, 2-chloro-5-(aminomethyl)thiophene, 2-aminomethylpyrrole, 3-aminomethylpyrrole, 2-(aminomethyl)oxazole, 4-(aminomethyl)oxazole, 5-(aminomethyl)isoxazole, 5-(aminomethyl)isothiazole, 4-(aminomethyl)isothiazole, 4-(aminomethyl-1H-imidazole, 2-(aminomethyl)-1H-imidazole, 5-(aminomethyl)pyrazole, 4-(aminomethyl)pyrazole, 4-(aminomethyl)pyridazine, 5-(aminomethyl)pyrimidine, 2-(aminomethyl)pyrazine, 2-(aminomethyl)quinoline, 7-chloro-2-aminomethylquinoline, 2-chloro-3-aminomethylquinoline, 2-(aminomethyl)-3-methylquinoxaline, 2-aminomethylbenzimidazole, 2-aminomethyl-5-chlorobenzimidazole, 3,4-methylenedioxybenzylamine, and the like.

Hereinafter, the present invention is explained in more detail by using Examples to which the present invention is not limited. For analyses, a gas chromatography (GC) method and a high performance liquid chromatography (LC) method were used.

EXAMPLE 1

Into a glass autoclave, 25.57 parts by weight of benzyl chloride (content: 99.0 wt %), 19.57 parts by weight of paraformaldehyde (content: 92 wt %) and 113.5 parts by weight of a 12 wt % ammonia/methanol solution were charged, and reacted under stirring at an internal temperature of 40° C. for 3 hours, 50° C. for 2 hours and 70° C. for 1 hour. The maximum value of the internal pressure (gauge pressure) during the reaction was 0.08 MPa. The resulting reaction liquid and methanol rinse were transferred into a four-neck flask, subjected to reduced pressure to remove ammonium remaining in the reaction liquid, and further concentrated to remove methanol. To the residual liquid thus obtained was added 200 parts by weight of water, and methanol was distilled off together with water under reduced pressure. The residue was subjected to an extraction/separation treatment using 150 parts by weight of toluene to obtain 161.9 parts by weight of a toluene solution containing 1,3,5-tris(benzyl)-1,3,5-hexahydrotriazine. To the toluene solution were added 50 parts by weight of water, 68.5 parts by weight of a 24 wt % aqueous solution of hydroxylamine sulfate and 20.9 parts by weight of 35 wt % hydrochloric acid, and the mixture was stirred at room temperature for 1 hour. The mixture was adjusted to pH 13 by an addition of 103.6 parts by weight of a 27 wt % sodium hydroxide aqueous solution, and then subjected to an extraction treatment to obtain an organic layer and an aqueous layer. The separated aqueous layer was further extracted with 80 parts by weight of toluene, and the organic layer was combined with the previously obtained organic layer to obtain 233.3 parts by weight of a solution containing benzylamine. The yield of benzylamine was 85.6% (GC method; based on benzyl chloride).

COMPARATIVE EXAMPLE 1

Into a stainless autoclave, 6.33 pars by weight of benzyl chloride (content: 99.0 wt %) and 30.4 parts by weight of a 12 wt % ammonia/methanol solution were charged, and were reacted under stirring at an internal temperature of 40° C. for 3 hours, 50° C. for 2 hours and 70° C. for 1 hour. The resulting reaction liquid and methanol rinse gave 126 parts by weight of a solution. The yield of benzylamine was 2.4% (GC method; based on benzyl chloride).

EXAMPLE 2

Into a stainless autoclave, 9.18 parts by weight of 3-chlorobenzyl chloride (content: 99.2 wt %), 5.59 parts by weight of paraformaldehyde (content: 92 wt %) and 40.39 parts by weight of a 12 wt % ammonia/methanol solution were charged, and reacted under stirring at an internal temperature of 70° C. for 3 hours. The maximum value of the internal pressure (gauge pressure) during the reaction was 0.08 MPa. The resulting reaction liquid and methanol rinse were transferred into a four-neck flask, subjected to reduced pressure to remove ammonium remaining in the reaction liquid, and further concentrated to remove methanol. To 21.05 parts by weight of the residual liquid thus obtained were added 24 parts by weight of water and 40 parts by weight of toluene, and an extraction/separation treatment was performed to obtain 45.48 parts by weight a toluene solution containing 1,3,5-tris(3-chlorobenzyl)-1,3,5-hexahydrotriazine.

A part of the toluene solution was concentrated under reduced pressure, and then subjected to column purification using hexane-ethyl acetate as a developing solvent to obtain 1,3,5-tris(3-chlorobenzyl)-1,3,5-hexahydrotriazine.

$^1$H-NMR(CDCl$_3$, 270 MHz, δ/ppm) 3.39 (brs, 2H), 3.63 (s, 2H), 7.1-7.4 (m, 4H)

$^{13}$C-NMR (CDCl$_3$, 75 MHz, δ/ppm) 56.41, 73.62, 126.81, 127.33, 128.66, 129.53, 134.23, 140.55

FD-MS m/z 459 M$^+$

At room temperature, 2.07 parts by weight of 1,3,5-tris(3-chlorobenzyl)-1,3,5-hexahydrotriazine, 15 parts by weight of toluene, 5.04 parts by weight of a 24 wt % aqueous hydroxylamine sulfate solution and 1.40 parts by weight of 35 wt % hydrochloric acid were stirred for 30 minutes. The mixture was adjusted to pH 13.1 by an addition of 6.16 parts by weight of a 27 wt % aqueous sodium hydroxide solution, and then subjected to a phase separation treatment to obtain a toluene layer containing 3-chlorobenzylamine and an aqueous layer. The aqueous layer thus obtained was extracted twice with 10 parts by weight and 5 parts by weight of toluene, and the obtained toluene layers were combined with the previously obtained toluene layer to obtain 31.50 parts by weight of a toluene solution containing 3-chlorobenzylamine (content: 5.21 wt %; GC method). The yield of 3-chlorobenzylamine was 86.1% (based on 1,3,5-tris(3-chlorobenzyl)-1,3,5-hexahydrotriazine).

EXAMPLE 3

Into a stainless autoclave, 9.17 parts by weight of 3-chlorobenzyl chloride (content: 99.2 wt %), 5.59 parts by weight of paraformaldehyde (content: 92 wt %) and 40.39 parts by weight of a 12 wt % ammonia/methanol solution were charged, and then reacted under stirring at an internal temperature of 70° C. for 3 hours. The maximum value of the internal pressure (gauge pressure) during the reaction was 0.08 MPa. The resulting reaction liquid was transferred together with methanol rinse into an eggplant shaped flask, subjected to reduced pressure to remove ammonium remaining in the reaction liquid, and further concentrated to remove methanol. Thus 18.43 parts by weight of the residual liquid was obtained. To 16.28 parts by weight of the residual liquid were added 10 parts by weight of water and 60 parts by weight of chloroform, and an extraction/separation treatment was performed to obtain 75.08 parts by weight of a chloroform solution containing 1,3,5-tris(3-chlorobenzyl)-1,3,5-hexahydrotriazine.

To the solution thus obtained were added 17.17 parts by weight of a 24 wt % aqueous hydroxylamine sulfate solution and 5.23 parts by weight of 35 wt % hydrochloric acid, and the mixture was stirred at room temperature for 30 minutes. The mixture was adjusted to pH 13 by an addition of 26.03 parts by weight of a 27 wt % aqueous sodium hydroxide solution, and then subjected to a phase separation treatment to obtain a chloroform layer containing 3-chlorobenzylamine and an aqueous layer. The aqueous layer thus obtained was extracted twice with chloroform, and the obtained chloroform layers were combined with the previously obtained chloroform layer to obtain 134.68 parts by weight of a chloroform solution containing 3-chlorobenzylamine (content: 3.86 wt %; GC method). The yield of 3-chlorobenzylamine was 73.7% (based on 3-chlorobenzyl chloride).

EXAMPLE 4

Into a stainless autoclave, 9.17 parts by weight of 3-chlorobenzyl chloride (content: 99.2 wt %), 5.58 parts by weight of paraformaldehyde (content: 92 wt %) and 40.37 parts by weight of a 12 wt % ammonia/methanol solution were charged, and reacted under stirring at an internal temperature of 70° C. for 3 hours. The maximum value of the internal pressure (gauge pressure) during the reaction was 0.08 MPa. The resulting reaction liquid was transferred together with methanol rinse into an eggplant shaped flask, subjected to reduced pressure to remove ammonium remaining in the reaction liquid, and further concentrated to remove methanol. Thus 21.29 parts by weight of the residual liquid was obtained. To the residual liquid were added 44.98 parts by weight of methanol and 19.58 parts by weight of 35% wt hydrochloric acid. The mixture was refluxed at an internal temperature of about 60° C. for 1.5 hours, cooled to an internal temperature of 40° C. or below, and then concentrated under reduced pressure to obtain 51.26 parts by weight of a residual liquid. To the residual liquid were added 25.1 parts by weight of toluene and 39.0 parts by weight of a 27 wt % aqueous sodium hydroxide solution. After adjusted to pH 13.2, the mixture was subjected to an extraction treatment to obtain an organic layer and an aqueous layer. The aqueous layer was extracted twice with toluene. The obtained toluene layers were combined with the previously obtained organic layer to obtain 63.64 parts by weight of a solution containing 3-chlorobenzylamine (content: 9.80 wt %; GC method). The yield of 3-chlorobenzylamine was 77.4% (based on 3-chlorobenzyl chloride).

EXAMPLE 5

Into a stainless autoclave, 8.91 parts by weight of 4-methoxybenzyl chloride, 5.57 parts by weight of paraformaldehyde (content: 92 wt %) and 40.37 parts by weight of a 12 wt % ammonia/methanol liquid were charged, and reacted under stirring at an internal temperature of 70° C. for 3 hours. The maximum value of the internal pressure (gauge pressure) during the reaction was 0.12 MPa. The resulting reaction liquid was transferred together with methanol rinse into an eggplant shaped flask, subjected to reduced pressure to remove ammonium remaining in the reaction liquid, and further concentrated to remove methanol. To 15.17 parts by weight of the residual liquid thus obtained were added 10 parts by weight of water and 59 parts by weight of chloroform, and an extraction/separation treatment was performed to obtain 66.38 parts by weight of a chloroform solution containing 1,3,5-tris(4-methoxybenzyl)-1,3,5-hexahydrotriazine.

To the solution thus obtained were added 17.17 parts by weight of a 24 wt % aqueous hydroxylamine sulfate solution and 5.23 parts by weight of 35 wt % hydrochloric acid, and the mixture was stirred at room temperature for 30 minutes. The mixture was adjusted to pH 13.4 by an addition of 25.13 parts by weight of a 27 wt % aqueous sodium hydroxide solution, and then subjected to a separation treatment to obtain a chloroform layer containing 4-methoxybenzylamine and an aqueous layer. The aqueous layer thus obtained was extracted twice with chloroform, and the obtained chloroform layers were combined with the previously obtained chloroform layer to obtain 140.59 parts by weight of a chloroform solution containing 4-methoxybenzylamine (content: 1.15 wt %; GC method). The yield of 4-methoxybenzylamine was 20.8% (based on 3-chlorobenzyl chloride).

EXAMPLE 6

Into a stainless autoclave, 9.34 parts by weight of 3-(chloromethyl)pyridine hydrochloride, 5.59 parts by weight of paraformaldehyde (content: 92 wt %) and 48.49 parts by weight of a 12 wt % ammonia/methanol solution were charged, and then reacted under stirring at an internal temperature of 70° C. for 3 hours. The maximum value of the internal pressure (gauge pressure) during the reaction was 0.08 MPa. The resulting reaction liquid was transferred together with methanol rinse into an eggplant shaped flask, subjected to reduced pressure to remove ammonium remaining in the reaction liquid, and further concentrated to remove methanol. To 17.49 parts by weight of the residual liquid thus obtained were added 100 parts by weight of methanol, 30 parts by weight of water and 5.94 parts by weight of 35% wt hydrochloric acid, and a hydrolysis treatment was performed to obtain 151.31 parts by weight of a solution containing 3-aminomethylpyridine (content: 3.06; LC method). The yield of 3-aminomethylpyridine was 75.3% (based on 3-(chloromethyl)pyridine hydrochloride).

COMPARATIVE EXAMPLE 2

This comparative example was performed in a similar manner as in Example 6 except that paraformaldehyde was not used. The maximum value of an internal pressure (gauge pressure) during the reaction was 0.10 MPa. The yield of 3-picolylamine was 30.2% (based on 3-(chloromethyl)pyridine hydrochloride; LC method).

INDUSTRIAL APPLICABILITY

According to the present invention, a selective and industrially advantageous method for producing a primary amine can be provided.

The invention claimed is:

1. A method for producing a primary amine compound represented by the formula (3):

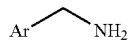
(3)

wherein Ar is as defined below,
which comprises reacting a halogen compound represented by the formula (1):

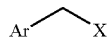
(1)

wherein Ar represents an aromatic group selected from the group consisting of a phenyl group, a naphthyl group, a pyridyl group, a furyl group, a thienyl group, a pyrrolyl group, an oxazolyl group, an isoxazolyl group, an isothiazolyl group, an imidazolyl group, a pyrazolyl group, a pyridazinyl group, a pyrimidinyl group, a pyrazinyl group, a quinolinyl group, a quinoxalinyl group and a benzimidazolyl group, and said Ar may have 1 to 3 substituents which may be the same or different and are independently a halogen atom, a lower alkyl group, a lower alkoxy group, a lower alkylenedioxy group, a nitro group, a cyano group or a di(lower alkyl amino group, and X represents a halogen atom, with ammonia and formaldehyde in an alcohol solvent to obtain a hexahydrotriazine compound represented by the formula (2):

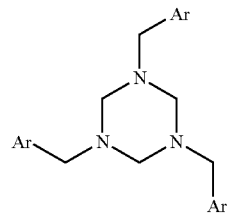
(2)

wherein Ar is as defined above, and
subjecting the hexahydrotriazine compound represented by the formula (2) to a decomposition treatment; and
wherein the decomposition treatment is conducted by reacting the hexahdrotrazine compound represented by the formula (2) with hydroxylamine under an acidic condition, and wherein 1 to 10 moles of formaldehyde is used per mole of the halogen compound represented by the formula (1).

2. The method according to claim 1, wherein formaldehyde is paraformaldehyde or formalin.

3. The method according to claim 1, wherein 1 to 30 moles of ammonia is used per mole of the halogen compound represented by the formula (1).

4. The method according to claim 1, wherein 1 to 10 moles of hydroxylamine is used per mole of the hexahydrotriazine compound represented by the formula (2).

5. The method according to claim 1 or 4, which comprises steps of subjecting the reaction mixture obtained by reacting the hexahydrotriazine compound represented by the formula (2) with hydroxylamine to a extraction treatment with a hydrophobic organic solvent under a basic condition, and then separating an organic layer containing the primary amine compound represented by the formula (3).

* * * * *